(12) United States Patent
Simonnet et al.

(10) Patent No.: US 8,834,903 B2
(45) Date of Patent: Sep. 16, 2014

(54) NANOEMULSION BASED ON SUGAR FATTY ESTERS OR ON SUGAR FATTY ETHERS AND ITS USES IN THE COSMETICS, DERMATOLOGICAL AND/OR OPHTHALMOLOGICAL FIELDS

(75) Inventors: Jean-Thierry Simonnet, Paris (FR); Odile Sonneville, Paris (FR); Sylvie Legret, Chatillon (FR)

(73) Assignee: L'Oreal, Paris (FR)

( * ) Notice: Subject to any disclaimer, the term of this patent is extended or adjusted under 35 U.S.C. 154(b) by 2197 days.

(21) Appl. No.: 10/724,826

(22) Filed: Dec. 2, 2003

(65) Prior Publication Data

US 2004/0076598 A1 Apr. 22, 2004

Related U.S. Application Data

(63) Continuation of application No. 09/460,092, filed on Dec. 13, 1999, now Pat. No. 6,689,371.

(30) Foreign Application Priority Data

Dec. 14, 1998 (FR) ..................... 98 15765

(51) Int. Cl.
| | |
|---|---|
| *A61K 8/02* | (2006.01) |
| *A61Q 5/00* | (2006.01) |
| *A61K 8/60* | (2006.01) |
| *A61K 8/06* | (2006.01) |
| *A61Q 19/00* | (2006.01) |
| *B82Y 5/00* | (2011.01) |
| *A61Q 1/14* | (2006.01) |

(52) U.S. Cl.
CPC ............... *A61Q 19/007* (2013.01); *A61Q 5/00* (2013.01); *A61K 2800/21* (2013.01); *A61Q 1/14* (2013.01); *Y10S 514/938* (2013.01); *A61K 8/60* (2013.01); *A61K 8/06* (2013.01); *A61K 2800/413* (2013.01); *A61Q 19/00* (2013.01); *A61K 8/602* (2013.01); *B82Y 5/00* (2013.01)
USPC .......................................... 424/401; 514/938

(58) Field of Classification Search
USPC ....................................................... 424/401
See application file for complete search history.

(56) References Cited

U.S. PATENT DOCUMENTS

| | | | | |
|---|---|---|---|---|
| 5,011,922 | A | * | 4/1991 | Matsumoto et al. ........... 536/119 |
| 5,130,122 | A | * | 7/1992 | Tabibi et al. ..................... 424/49 |
| 5,266,321 | A | * | 11/1993 | Shukuzaki et al. ............. 424/401 |
| 5,412,004 | A | * | 5/1995 | Tachibana et al. ............... 524/27 |
| 5,658,575 | A | | 8/1997 | Ribier et al. |
| 5,698,219 | A | * | 12/1997 | Valdivia et al. ................ 424/450 |
| 5,753,241 | A | * | 5/1998 | Ribier et al. .................... 424/401 |
| 5,925,341 | A | * | 7/1999 | Cervantes et al. .......... 424/78.03 |
| 5,925,364 | A | * | 7/1999 | Ribier et al. .................... 424/401 |
| 6,066,328 | A | * | 5/2000 | Ribier et al. .................... 424/401 |
| 6,117,415 | A | * | 9/2000 | Schwarz ........................... 424/49 |
| 6,120,778 | A | * | 9/2000 | Simonnet ....................... 424/401 |
| 6,126,948 | A | | 10/2000 | Simonnet et al. |
| 6,153,569 | A | * | 11/2000 | Halloran ........................ 510/119 |
| 6,274,150 | B1 | | 8/2001 | Simonnet et al. |
| 6,335,022 | B1 | | 1/2002 | Simonnet et al. |
| 6,375,960 | B1 | | 4/2002 | Simonnet et al. |
| 6,413,527 | B1 | | 7/2002 | Simonnet et al. |
| 6,419,946 | B1 | | 7/2002 | Sonneville et al. |
| 6,461,625 | B1 | | 10/2002 | Simonnet et al. |
| 6,464,990 | B2 | | 10/2002 | Simonnet et al. |
| 6,541,018 | B1 | | 4/2003 | Simonnet et al. |
| 6,562,356 | B2 | * | 5/2003 | Verite et al. .................... 424/401 |
| 6,669,849 | B1 | * | 12/2003 | Nguyen et al. ................. 210/638 |
| 2004/0009131 | A1 | * | 1/2004 | Simonnet et al. ............... 424/63 |
| 2004/0258644 | A1 | * | 12/2004 | Simonnet ...................... 424/70.9 |
| 2005/0226842 | A1 | * | 10/2005 | Douin et al. ................. 424/70.28 |
| 2006/0030655 | A1 | * | 2/2006 | L'Alloret et al. .............. 524/315 |
| 2006/0193813 | A1 | * | 8/2006 | Simonnet ................... 424/70.21 |
| 2007/0027034 | A1 | * | 2/2007 | Tank et al. ..................... 504/363 |

FOREIGN PATENT DOCUMENTS

EP          728460          8/1996

OTHER PUBLICATIONS wikipedia.org entry for Jojoba oil on Mar. 13, 2007. http://en.wikipedia.org/wiki/Jojoba_oil.*
WP Index Abstract of EP-728460A1 (Aug. 1996), AN: 1996-394823, Legret.
U.S. Appl. No. 09/903,768, filed Jul. 13, 2001, L'Alloret, et al.
U.S. Appl. No. 09/848,412, filed May 4, 2001, Sonneville-Aubrun, et al.
U.S. Appl. No. 09/860,466, filed May 21, 2001, Sonneville-Aubrun, et al.
U.S. Appl. No. 10/207,396, filed Jul. 30, 2002, Simmonet, et al.

* cited by examiner

*Primary Examiner* — Snigdha Maewall
(74) *Attorney, Agent, or Firm* — Oblon, Spivak, McClelland, Maier & Neustadt, L.L.P.

(57) ABSTRACT

A nanoemulsion, the oily globules of which have a number-average size of less than 100 nm, comprising a surfactant which is solid at a temperature of less than or equal to 45° C., which surfactant is chosen from esters of a fatty acid and of a sugar and ethers of a fatty alcohol and of a sugar, and at least one oil having a molecular weight of greater than 400, the ratio by weight of the amount of oily phase to the amount of surfactant ranging from 2 to 10. The nanoemulsion may be used for cosmetics and dermatological applications, in particular for moisturizing the skin and/or mucous membranes, as well as for treating the hair, and in the ophthalmological field, as an eye lotion for treating the eyes.

27 Claims, No Drawings

NANOEMULSION BASED ON SUGAR FATTY ESTERS OR ON SUGAR FATTY ETHERS AND ITS USES IN THE COSMETICS, DERMATOLOGICAL AND/OR OPHTHALMOLOGICAL FIELDS

BACKGROUND OF THE INVENTION

1. Field of the Invention

The present invention relates to a nanoemulsion based on a surfactant which is solid at a temperature of less than or equal to 45° C., which surfactant is chosen from esters of a fatty acid and of a sugar and ethers of a fatty alcohol and of a sugar, and on at least one oil having a molecular weight of greater than 400, the ratio by weight of the amount of oily phase to the amount of surfactant ranging from 2 to 10.

The invention also relates to a process for the preparation of the said nanoemulsion and to its uses in the cosmetics, dermatological and/or ophthalmological fields. This nanoemulsion is stable on storage and can comprise large amounts of oil while retaining good transparency and while having good cosmetic properties.

2. Description of the Background

Nanoemulsions are oil-in-water emulsions, the oil globules of which have a very fine particle size, that is to say a number-average size of less than 100 nm. They are generally manufactured by mechanical fragmentation of an oily phase in an aqueous phase in the presence of a surfactant. In the case of nanoemulsions, the very small size of the oily globules is obtained in particular by virtue of at least one pass through a high-pressure homogenizer. The small size of the globules confers on them cosmetically advantageous properties which distinguish them from conventional emulsions: they are transparent and exhibit a novel texture. They can also carry active agents more efficiently.

Transparent microemulsions are known in the state of the art. In contrast to nanoemulsions, microemulsions are not, strictly speaking, emulsions; they are transparent solutions of micelles swollen by oil, which oil is generally a very-short-chain oil (e.g. hexane or decane) and is solubilized by virtue of the joint presence of a significant amount of surfactants and of cosurfactants which form the micelles. The size of the swollen micelles is very small owing to the small amount of oil which they can solubilize. This very small size of the micelles is the cause of their transparency, as with nanoemulsions. However, in contrast to nanoemulsions, microemulsions are spontaneously formed by mixing the constituents, without contributing mechanical energy other than simple magnetic stirring. The major disadvantages of microemulsions are related to their high proportion of surfactants, leading to intolerance and resulting in a sticky feel during application to the skin. Furthermore, their formulation range is generally very narrow and their temperature stability very limited.

In addition, nanoemulsions are known in the state of the art comprising an amphiphilic lipid phase composed of phospholipids, water and oil. These emulsions exhibit the disadvantage of being unstable on storage at conventional storage temperatures, namely between 0 and 45° C. They lead to yellow compositions and produce rancid smells which develop after several days of storage.

Nanoemulsions stabilized by a lamellar liquid crystal coating, obtained by the combination of a hydrophilic surfactant and of a lipophilic surfactant, are also known. However, these combinations are problematic to prepare. Furthermore, the nanoemulsions obtained exhibit a waxy and film-forming feel which is not very pleasant for the user.

Furthermore, the document EP-A-728,460 discloses nanoemulsions based on fluid non-ionic amphiphilic lipids. However, these nanoemulsions exhibit the disadvantage of having a sticky effect during application to the skin.

The need therefore remains for nanoemulsions which have neither the disadvantages of those of the prior art nor the disadvantages of microemulsions.

SUMMARY OF THE INVENTION

The present inventors have now discovered, unexpectedly, that the use of a surfactant which is solid at a temperature of less than or equal to 45° C., which surfactant is chosen from sugar esters or ethers, and of at least one oil having a molecular weight of greater than 400 (that is to say, 400 grams per mole) makes it possible to obtain novel nanoemulsions exhibiting all the advantages of known nanoemulsions without their disadvantages.

Accordingly, the present invention relates to a nanoemulsion, comprising:
  an oily phase dispersed in an aqueous phase and having oil globules with a number-average size of less than 100 nm,
  a surfactant which is solid at a temperature of less than or equal to 45° C., wherein the surfactant is selected from the group consisting of esters of a fatty acid and of a sugar and ethers of a fatty alcohol and of a sugar, and
  at least one oil having a molecular weight of greater than 400,
  where the ratio by weight of the amount of oily phase to the amount of surfactant is 2 to 10.

The present invention also provides a method of caring for, treating and/or making up the skin, face and/or scalp, comprising applying the nanoemulsion to the skin, face and/or scalp.

The present invention also provides a method of caring for and/or treating the hair, comprising applying the nanoemulsion to the hair.

The present invention also provides a method of caring for and/or moisturizing the skin, mucous membranes and/or scalp, comprising applying the nanoemulsion to the skin, mucous membranes and/or scalp.

The present invention also provides a method of preparing the nanoemulsion.

A more complete appreciation of the invention and many of the attendant advantages thereof will be readily obtained as the same becomes better understood by reference to the following detailed description.

DETAILED DESCRIPTION OF THE INVENTION

The nanoemulsions according to the invention generally have a transparent to bluish appearance. Their transparency is measured by a transmittance coefficient at 600 nm ranging from 10 to 90% or else by a turbidity ranging from 60 to 600 NTU and preferably from 70 to 300 NTU, which turbidity is measured with a Hach Model 2100 P portable turbidimeter. This range for the transparency includes all specific values and subranges therebetween, such as 20%, 30%, 50%, 75% and 85%. This range for the turbidity includes all specific values and subranges therebetween, such as 80, 90, 125, 150, 200 and 250 NTU.

The oil globules of the nanoemulsions of the invention have a number-average size of less than 100 nm and preferably ranging from 20 to 75 nm and more preferably from 40 to 60 nm. This range includes all specific values and subranges therebetween, such as 25, 30, 50, 80 nm. The decrease in the size of the globules makes it possible to promote the penetration of the active principles into the surface layers of the skin (carrier effect).

The surfactant which is solid at a temperature of less than or equal to 45° C. which can be used in the nanoemulsion of the invention is chosen exclusively from esters of a fatty acid and of a sugar, ethers of a fatty alcohol and of a sugar, and their mixtures, which means that the nanoemulsion of the invention is devoid of any surfactant other than sugar fatty esters or fatty ethers.

The esters of a fatty acid and of a sugar which can be used as surfactants in the nanoemulsions according to the invention are solid at a temperature of less than or equal to 45° C. and can be chosen in particular from the group consisting of esters or mixtures of esters of a $C_8$-$C_{22}$ fatty acid and of sucrose, maltose, glucose or fructose and esters or mixtures of esters of a $C_{14}$-$C_{22}$ fatty acid and of methylglucose.

The $C_8$-$C_{22}$ or $C_{14}$-$C_{22}$ fatty acids which form the fatty unit of the esters which can used in the nanoemulsion of the invention comprise a saturated or unsaturated linear alkyl chain respectively comprising from 8 to 22 or from 14 to 22 carbon atoms. The fatty unit of the esters can be chosen in particular from stearates, behenates, arachidonates, palmitates, myristates, laurates, caprates and their mixtures. Stearates are preferably used.

Mention may be made, by way of examples of esters or of mixtures of esters of a fatty acid and of sucrose, maltose, glucose or fructose, of sucrose monostearate, sucrose distearate, sucrose tristearate and their mixtures, such as the products sold by Croda under the name Crodesta F50, F70, F110 and F160, respectively having an HLB (Hydrophilic Lipophilic Balance) of 5, 7, 11 and 16; and, by way of examples of esters or of mixtures of esters of a fatty acid and of methylglucose, of the distearate of methylglucose and of polyglycerol-3 sold by Goldschmidt under the name of Tego-care 450. Mention may also be made of glucose or maltose monoesters, such as methyl O-hexadecanoyl-6-D-glucoside and methyl O-hexadecanoyl-6-D-maltoside.

The ethers of a fatty alcohol and of a sugar which can be used as surfactants in the nanoemulsion according to the invention are solid at a temperature of less than or equal to 45° C. and can be chosen in particular from the group consisting of ethers or mixtures of ethers of a $C_8$-$C_{22}$ fatty alcohol and of glucose, maltose, sucrose or fructose and ethers or mixtures of ethers of a $C_{14}$-$C_{22}$ fatty alcohol and of methylglucose. They are in particular alkyl polyglucosides.

The $C_8$-$C_{22}$ or $C_{14}$-$C_{22}$ fatty alcohols which form the fatty unit of the ethers which can be used in the nanoemulsion of the invention comprise a saturated or unsaturated linear alkyl chain respectively comprising from 8 to 22 or from 14 to 22 carbon atoms. The fatty unit of the ethers can in particular be chosen from the decyl, cetyl, behenyl, arachidyl, stearyl, palmityl, myristyl, lauryl, capryl or hexadecanoyl units and their mixtures, such as cetearyl.

Mention may be made, by way of examples of ethers of a fatty alcohol and of a sugar, of alkyl polyglucosides, such as decyl glucoside and lauryl glucoside, sold, for example, by Henkel under the respective names Plantaren 2000 and Plantaren 1200, cetostearyl glucoside, optionally as a mixture with cetostearyl alcohol, sold, for example, under the name Montanov 68 by Seppic, under the name Tego-care CG90 by Goldschmidt and under the name Emulgade KE 3302 by Henkel, and arachidyl glucoside, for example in the form of the mixture of arachidyl and behenyl alcohols and of arachidyl glucoside sold under the name Montanov 202 by Seppic.

According to a specific embodiment of the invention, use is more particularly made, as surfactant, of sucrose monostearate, sucrose distearate, sucrose tristearate and their mixtures, the distearate of methylglucose and of polyglycerol-3, and alkyl polyglucosides.

Depending on whether its character is more hydrophilic or more lipophilic, the surfactant can be introduced into the aqueous phase or into the oily phase of the nanoemulsion.

The amount of surfactant in the nanoemulsion of the invention can range, for example, from 0.2 to 15% by weight and preferably from 1 to 8% by weight with respect to the total weight of the nanoemulsion. These ranges include all specific values and subranges therebetween, such as 0.5, 1, 2, 5, 8, 10 and 12% by weight.

The ratio by weight of the amount of the oily phase to the amount of surfactant ranges from 2 to 10 and preferably from 3 to 6. This range includes all specific values and subranges therebetween, such as 4,5, and 8. The term "amount of oily phase" is understood here to mean the total amount of the constituents of this phase without including the amount of surfactant.

The nanoemulsion according to the invention comprises at least one oil with a molecular weight of greater than 400. The oils with a molecular weight of greater than 400 can be chosen from oils of animal or vegetable origin, mineral oils, synthetic oils and silicone oils, and their mixtures. Mention may be made, as oils of this type, of, for example, isocetyl palmitate, isocetyl stearate, avocado oil or jojoba oil.

In addition, the oily phase can optionally comprise other oils and in particular oils having a molecular weight of less than 400. These oils are also chosen from oils of animal or vegetable origin, mineral oils, synthetic oils and silicone oils. Mention may be made, for example, as oils with a molecular weight of less than 400, of isododecane, isohexadecane, volatile silicone oils, isopropyl myristate, isopropyl palmitate or $C_{11}$-$C_{13}$ isoparaffin.

The oily phase can also comprise fatty substances other than the oils indicated above, such as fatty alcohols, for example stearyl, cetyl and behenyl alcohols, fatty acids, for example stearic, palmitic and behenic acids, oils of fluorinated type, waxes, gums and their mixtures.

The nanoemulsions in accordance with the invention comprise an amount of oily phase preferably ranging from 2 to 40% and better still from 5 to 30% by weight with respect to the total weight of the nanoemulsion, the proportion of oil(s) having a molecular weight of greater than 400 preferably representing at least 40% by weight of the oily phase. These ranges for the amount of oily phase include all specific values and subranges therebetween, such as 8, 10, 12, 15, 20, 25 and 35% by weight.

According to a specific embodiment of the invention, the nanoemulsion of the invention additionally comprises one or more ionic amphiphilic lipids.

The ionic amphiphilic lipids which can be used in the nanoemulsions of the invention are preferably chosen from the group formed by anionic amphiphilic lipids, cationic amphiphilic lipids and alkylsulfonic derivatives.

The anionic amphiphilic lipids can be more particularly chosen from the group formed by:
 the alkaline salts of dicetyl and dimyristyl phosphate;
 the alkaline salts of cholesterol sulphate;
 the alkaline salts of cholesterol phosphate;
 lipoamino acids and their salts, such as mono- and disodium acylglutamates, such as the disodium salt of N-stearoyl-L-glutamic acid sold under the name Acylglutamate HS21 by Ajinomoto;

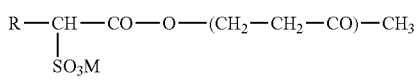

the sodium salts of phosphatidic acid;
phospholipids.

The alkylsulfonic derivatives can more particularly be chosen from the alkylsulfonic derivatives of formula (I):
in which R represents an alkyl radical comprising from 16 to 22 carbon atoms, in particular the $C_{16}H_{33}$ and $C_{18}H_{37}$ radicals, taken as a mixture or separately, and M is an alkali metal, such as sodium.

The cationic amphiphilic lipids can more particularly be chosen from the group formed by quaternary ammonium salts, fatty amines and their salts.

The quaternary ammonium salts are, for example:
those which exhibit the following general formula (II):

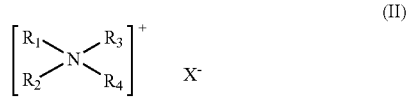

in which the $R_1$ to $R_4$ radicals, which can be identical or different, represent a linear or branched aliphatic radical comprising from 1 to 30 carbon atoms or an aromatic radical, such as aryl or alkylaryl. The aliphatic radicals can comprise heteroatoms, such as, in particular, oxygen, nitrogen, sulphur or halogens. The aliphatic radicals are, for example, chosen from alkyl, alkoxy, polyoxy($C_2$-$C_6$)alkylene, alkylamido, ($C_{12}$-$C_{22}$)alkylamido($C_2$-$C_6$)alkyl, ($C_{12}$-$C_{22}$)alkyl acetate or hydroxyalkyl radicals comprising approximately from 1 to 30 carbon atoms; X is an anion chosen from the group of the halides, phosphates, acetates, lactates, ($C_2$-$C_6$)alkyl sulphates, or alkyl- or alkylarylsulphonates. Preference is given, as quaternary ammonium salts of formula (II), to, on the one hand, tetraalkylammonium chlorides, such as, for example, dialkyldimethylammonium or alkyltrimethylammonium chlorides in which the alkyl radical comprises approximately from 12 to 22 carbon atoms, in particular behenyltrimethylammonium, distearyldimethylammonium, cetyltrimethylammonium and benzyldimethylstearylammonium chlorides, or alternatively, on the other hand, stearamidopropyldimethyl(myristyl acetate)ammonium chloride, sold under the name "Ceraphyl 70" by Van Dyk.

imidazolinium quaternary ammonium salts, such as, for example, those of following formula (III):

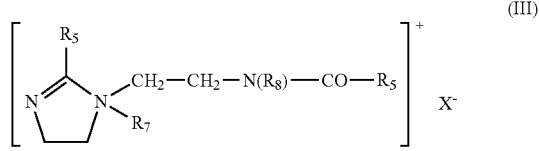

in which $R_5$ represents an alkenyl or alkyl radical comprising from 8 to 30 carbon atoms, for example derived from tallow fatty acids; R represents a hydrogen atom, an alkyl radical comprising from 1 to 4 carbon atoms or an alkenyl or alkyl radical comprising from 8 to 30 carbon atoms; $R_7$ represents an alkyl radical comprising from 1 to 4 carbon atoms; $R_8$ represents a hydrogen atom or an alkyl radical comprising from 1 to 4 carbon atoms; and X is an anion chosen from the group of the halides, phosphates, acetates, lactates, alkyl sulphates, or alkyl- or alkylarylsulphonates. $R_5$ and $R_6$ preferably denote a mixture of alkenyl or alkyl radicals comprising from 12 to 21 carbon atoms, for example derived from tallow fatty acids, $R_7$ preferably denotes a methyl radical and $R_8$ preferably denotes hydrogen. Such a product is, for example, sold under the name "Rewoquat W 75" by Rewo.

quaternary diammonium salts of formula (IV):

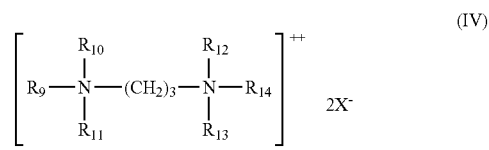

in which $R_9$ denotes an aliphatic radical comprising approximately from 16 to 30 carbon atoms; $R_{10}$, $R_{11}$, $R_{12}$, $R_{13}$ and $R_{14}$ are chosen from hydrogen or an alkyl radical comprising from 1 to 4 carbon atoms; and X is an anion chosen from the group of the halides, acetates, phosphates, nitrates and methyl sulphates.

Such quaternary diammonium salts comprise in particular propanetallowdiammonium dichloride.

According to a preferred embodiment of the invention, a lipoamino acid is used as ionic amphiphilic lipid.

The ionic amphiphilic lipids can be introduced into one or other phase of the nanoemulsion. When they are present in the nanoemulsion of the invention, they can be used in concentrations preferably ranging from 0.01 to 5% by weight and more particularly from 0.25 to 1% by weight with respect to the total weight of the nanoemulsion.

The emulsions in accordance with the present invention can comprise additives for improving the transparency of the formulation.

These additives are preferably chosen from the group formed by:
lower alcohols comprising from 1 to 8 carbon atoms and more particularly from 2 to 6 carbon atoms, such as ethanol;
glycols, such as glycerol, propylene glycol, 1,3-butylene glycol, dipropylene glycol, pentylene glycol, isoprene glycol and polyethylene glycols comprising from 4 to 16 and preferably from 8 to 12 ethylene oxide units;
sugars, such as glucose, fructose, maltose, lactose or sucrose.

These additives can be used as a mixture. When they are present in the nanoemulsion of the invention, they can be used at concentrations preferably ranging from 0.01 to 30% by weight with respect to the total weight of the nanoemulsion and better still from 5 to 20% by weight with respect to the total weight of the nanoemulsion. This range includes all specific values and subranges therebetween, such as 0.02, 0.05, 0.5, 1, 2, 10, 15 and 25% by weight. The amount of alcohol(s) and/or of sugar(s) preferably ranges from 5 to 20% by weight with respect to the total weight of the nanoemulsion and the amount of glycol(s) preferably ranges from 5 to 15% by weight with respect to the total weight of the nanoemulsion.

In addition, the use of the alcohols as defined above at concentrations greater than or equal to 15% by weight makes it possible to obtain preservative-free emulsions.

The nanoemulsions defined above can constitute compositions for topical use and in particular cosmetic or dermatological compositions. They can also be used as ophthalmic vehicles.

Also included in the scope of the invention is, therefore, a composition for topical use, characterized in that it is composed of a nanoemulsion as defined above. A composition for topical use comprises a physiologically acceptable medium, that is to say compatible with the skin, mucous membranes, scalp, eyes and/or hair.

Another aspect of the invention is an ophthalmic vehicle, characterized in that it is composed of a nanoemulsion as defined above.

The nanoemulsions of the invention can comprise water-soluble or fat-soluble active principles having a cosmetic, dermatological or ophthalmic activity. The fat-soluble active principles are in the oily globules of the emulsion, whereas the water-soluble active principles are in the aqueous phase of the emulsion. Mention may be made, by way of examples of active principles, of vitamins, such as vitamin E, and their derivatives and in particular their esters, provitamins, such as panthenol, humectants and sun-screen agents.

Mention may be made, as ophthalmic active principles, of, for example, antiglaucoma agents, such as betaxolol; antibiotics, such as acyclovir; antiallergics; anti-inflammatory agents, such as ibuprofen and its salts, diclofenac and its salts, or indomethacin; or antiviral agents.

The nanoemulsions in accordance with the invention can be provided in the form of a lotion, serum, cream, milk or toilet water and can comprise adjuvants commonly used in the cosmetics, dermatological and ophthalmic fields, such as, for example, gelling agents, preservatives, antioxidants and fragrances. They can also be provided in the form of an eye lotion, in particular for ophthalmological applications.

Mention may be made, among the gelling agents which can be used, of cellulose derivatives, algal derivatives, natural gums and synthetic polymers, such as polymers and copolymers of carboxyvinyl acids, for example those sold under the name Carbopol by Goodrich.

Another subject-matter of the invention is a process for the preparation of a nanoemulsion as defined above, this process comprising the mixing of the aqueous phase and the oily phase with vigorous stirring at a temperature ranging from 10 to 80° C. and then a homogenization of the mixture at a pressure preferably ranging from $6 \times 10^7$ Pa to $18 \times 10^7$ Pa (high-pressure homogenization). The shearing preferably ranges from $2 \times 10^6$ s$^{-1}$ to $5 \times 10^8$ s$^{-1}$ and better still from $1 \times 10^8$ s$^{-1}$ to $3 \times 10^8$ s$^{-1}$ (s$^{-1}$ signifies second$^{-1}$).

The nanoemulsion of the invention can be used, for example, for caring for, treating or making up the skin, face and/or scalp.

Another subject-matter of the invention is therefore the cosmetic use of the nanoemulsion as defined above for caring for, treating and/or making up the skin, face and/or scalp.

In addition, the nanoemulsion of the invention can also be used for caring for and/or treating the hair. It makes it possible to obtain a deposit of oil on the hair, which renders the latter glossier and more resistant to styling, without, however, making it lank. It also makes it possible, as a pretreatment, to improve the effects of dyeing or permanent waving.

Another subject-matter of the invention is therefore the cosmetic use of the nanoemulsion as defined above for caring for and/or treating the hair.

The nanoemulsion according to the invention makes possible in particular good moisturizing of the skin, mucous membranes and/or scalp and is particularly suited to the treatment of dry skin.

Another subject-matter of the invention is therefore a cosmetic process for caring for and/or moisturizing the skin, mucous membranes and/or scalp, characterized in that a nanoemulsion as defined above is applied to the skin, mucous membranes and/or scalp.

The invention also relates to the use of the nanoemulsion according to the invention in the manufacture of a dermatological composition intended for the treatment of dry skin.

Regarding the uses described above, one skilled in the art will recognize that the compositions of the inventions are to be applied using amounts and techniques customary for the dermatological and cosmetic fields.

Finally, the invention also relates to the use of the nanoemulsion according to the invention in the manufacture of an ophthalmological composition.

EXAMPLES

Having generally described this invention, a further understanding can be obtained by reference to certain specific examples which are provided herein for purposes of illustration only and are not intended to be limiting unless otherwise specified. The amounts shown are as % by weight.

Example 1

Fluid Make-up Remover

Oily Phase:

| | |
|---|---|
| Tego-Care 450 (Company Goldschmidt) | 4.5% |
| Disodium salt of N-stearoyl-L-glutamic acid (Acylglutamate HS21 from Ajinomoto) | 0.5% |
| Isocetyl stearate (M.W. = 508) | 10% |
| Isopropyl myristate (M.W. = 270) | 5% |

Aqueous Phase:

| | |
|---|---|
| Glycerol | 5% |
| Dipropylene glycol | 10% |
| Water | 65% |

A transparent nanoemulsion is obtained, the size of the globules of which is 49 nm and the turbidity of which is 218 NTU.

Example 2

Make-up Removing Gel

Oily Phase:

| | |
|---|---|
| Crodesta F50 (Company Croda) | 4.5% |
| Disodium salt of N-stearoyl-L-glutamic acid (Acylglutamate HS21 from the company Ajinomoto) | 0.5% |
| Isocetyl stearate (M.W. = 508) | 20% |
| $C_{11}$-$C_{13}$ Isoparaffin (M.W. = 170) | 2.5% |
| Isohexadecane (M.W. = 226) | 2.5% |

Aqueous Phase:

| | |
|---|---|
| Glycerol | 5% |
| Dipropylene glycol | 10% |
| Water | 55% |

A gelled transparent nanoemulsion is obtained, the size of the globules of which is 45 nm and the turbidity of which is 260 NTU.

Example 3

Scented Water

Oily Phase:

| | |
|---|---|
| Crodesta F70 (Company Croda) | 4.5% |
| Disodium salt of N-stearoyl-L-glutamic acid (Acylglutamate HS21) (Company Ajinomoto) | 0.5% |
| Soybean oil (M.W. of the order of 900) | 6% |
| Volatile silicone oil (M.W. = 106) | 2% |
| Fragrance | 3% |
| Vitamin E acetate | 0.5% |
| Ethanol | 10% |

Aqueous Phase:

| | |
|---|---|
| Glycerol | 5% |
| Water | 68.5% |

A transparent nanoemulsion is obtained, the size of the globules of which is 39 nm and the turbidity of which is 96 NTU.

Example 4

Fluid Make-up Remover

Oily Phase:

| | |
|---|---|
| Tego-Care CG90 (Company Goldschmidt) | 4.5% |
| Disodium salt of N-stearoyl-L-glutamic acid (Acylglutamate HS21 from the company Ajinomoto) | 0.5% |
| Isocetyl stearate (M.W. = 508) | 10% |
| Isopropyl myristate (M.W. = 270) | 5% |

Aqueous Phase:

| | |
|---|---|
| Glycerol | 5% |
| Dipropylene glycol | 10% |
| Water | 65% |

A transparent nanoemulsion is obtained, the size of the globules of which is 43 nm and the turbidity of which is 145 NTU.

Example 5

Care Gel

Oily Phase:

| | |
|---|---|
| Montanov 68 (Company Seppic) | 4.5% |
| Disodium salt of N-stearoyl-L-glutamic acid (Acylglutamate HS21 from the company Ajinomoto) | 0.5% |
| Soybean oil (M.W. of the order of 900) | 9% |
| Avocado oil (M.W. of the order of 900) | 9% |
| Volatile silicone oil (M.W. = 106) | 6% |

Aqueous Phase:

| | |
|---|---|
| Glycerol | 5% |
| Dipropylene glycol | 10% |
| Water | 56% |

A gelled transparent nanoemulsion is obtained, the size of the globules of which is 46 nm and the turbidity of which is 240 NTU.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 98-15765, filed on Dec. 14, 1998, and incorporated herein by reference in its entirety.

The invention claimed is:

1. An oil-in-water nanoemulsion, comprising:
an oily phase dispersed in an aqueous phase and having oil globules with a number-average size of less than 100 nm, wherein the oil globules are free of a lamellar liquid crystal coating,
a surfactant which is solid at a temperature of less than or equal to 45° C., wherein the surfactant is selected from the group consisting of esters of a fatty acid and of a sugar and ethers of a fatty alcohol and of a sugar, and
an oily phase comprising 10% to 40% by weight with respect to the total weight of the nanoemulsion which comprises at least one oil having a molecular weight of greater than 400,
wherein the ratio by weight of the amount of oily phase to the amount of surfactant is 2 to 10, and wherein the nanoemulsion has a turbidity of 60 to 600 NTU.

2. The nanoemulsion of claim 1, wherein the amount of surfactant is 0.2 to 15% by weight with respect to the total weight of the nanoemulsion.

3. The nanoemulsion of claim 1, wherein the ratio by weight of the amount of oily phase to the amount of surfactant is 3 to 6.

4. The nanoemulsion of claim 1, wherein the oil globules have an average size of 20 to 75 nm.

5. The nanoemulsion of claim 1, wherein the surfactant is selected from the group consisting of esters or mixtures of esters of a $C_8$-$C_{22}$ fatty acid and of sucrose, maltose, glucose or fructose, esters or mixtures of esters of a $C_{14}$-$C_{22}$ fatty acid and of methylglucose, ethers or mixtures of ethers of a $C_8$-$C_{22}$ fatty alcohol and of glucose, maltose, sucrose or fructose, and ethers or mixtures of ethers of a $C_{14}$-$C_{22}$ fatty alcohol and of methylglucose.

6. The nanoemulsion of claim 1, wherein the surfactant is selected from the group consisting of sucrose monostearate, sucrose distearate, sucrose tristearate and their mixtures, the distearate of methylglucose and polyglycerol-3, and alkyl polyglucosides.

7. The nanoemulsion of claim 1, wherein the oil with a molecular weight of greater than 400 is selected from the group consisting of animal oils, vegetable oils, mineral oils, synthetic oils, silicone oils, and mixtures thereof.

8. The nanoemulsion of claim 1, wherein the oily phase additionally comprises at least one oil having a molecular weight of less than 400.

9. The nanoemulsion of claim 1, wherein the oily phase comprises at least 40% by weight of oil(s) having a molecular weight of greater than 400 with respect to the total weight of the oily phase.

10. The nanoemulsion of claim 1, further comprising at least one ionic amphiphilic lipid selected from the group consisting of anionic amphiphilic lipids, cationic amphiphilic lipids and alkylsulfonic derivatives, wherein the alkylsulfonic derivatives are of the formula (I):

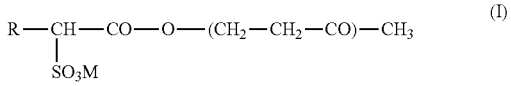

in which R represents $C_{16}$-$C_{22}$ alkyl radicals, taken as a mixture or separately, and M is an alkali metal.

11. The nanoemulsion according to claim 10, wherein the ionic amphiphilic lipids are selected from the group consisting of
the alkaline salts of dicetyl and dimyristyl phosphate;
the alkaline salts of cholesterol sulphate;
the alkaline salts of cholesterol phosphate;
the salts of lipoamino acids;
the sodium salts of phosphatidic acid;
phospholipids;
the alkylsulfonic derivatives of formula (I):

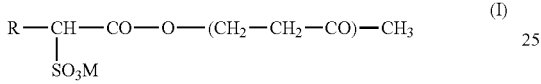

in which R represents $C_{16}$- $C_{22}$ alkyl radicals, taken as a mixture or separately, and M is an alkali metal;
quaternary ammonium salts, fatty amines and their salts; and mixtures thereof.

12. The nanoemulsion of claim 10, wherein the amount of ionic amphiphilic lipid(s) is 0.01 to 5% by weight with respect to the total weight of the nanoemulsion.

13. The nanoemulsion of claim 1, further comprising an additive which improves the transparency thereof and selected from the group consisting lower alcohols, glycols, sugars and mixtures thereof.

14. The nanoemulsion of claim 13, wherein the additive is present in a concentration ranging from 5 to 20% by weight with respect to the total weight of the nanoemulsion.

15. The nanoemulsion of claim 1, further comprising a cosmetic, dermatological or ophthalmological active agent.

16. A composition suitable for topical use comprising the nanoemulsion of claim 1.

17. An ophthalmic vehicle comprising the nanoemulsion of claim 1.

18. A method of caring for, treating and/or making up the skin, face and/or scalp, comprising applying the nanoemulsion of claim 1 to the skin, face and/or scalp.

19. A method of caring for and/or treating the hair, comprising applying the nanoemulsion of claim 1 to the hair.

20. A method of caring for and/or moisturizing the skin, mucous membranes and/or scalp, comprising applying the nanoemulsion of claim 1 to the skin, mucous membranes and/or scalp.

21. A method of preparing the nanoemulsion of claim 1, comprising:
mixing the aqueous phase and the oily phase with vigorous stirring at an ambient temperature ranging from 10 to 80° C. and then homogenizing the mixture at a pressure ranging from $6 \times 10^7$ Pa to $18 \times 10^7$ Pa.

22. The process of claim 21, wherein said mixing is conducted at a shearing of $2 \times 10^6 s^{-1}$ to $5 \times 10^8$ $s^{-1}$.

23. A method of caring for skin comprising applying the nanoemulsion according to claim 1 to the skin.

24. A method of treating skin comprising applying the nanoemulsion according to claim 1 to the skin.

25. A method of making up skin comprising applying the nanoemulsion according to claim 1 to the skin.

26. A method of caring for hair comprising applying the nanoemulsion according to claim 1 to the hair.

27. A method of treating hair comprising applying the nanoemulsion according to claim 1 to the hair.

* * * * *